United States Patent [19]

White et al.

[11] 3,931,226

[45] Jan. 6, 1976

[54] PROCESS FOR THE PREPARATION OF DIAZEPINO[1,2-A]INDOLES

[75] Inventors: Alan Chapman White, Windsor, England; Stanley Charles Bell, Penn Valley, Pa.

[73] Assignee: John Wyeth & Brother Limited, Maidenhead, England

[22] Filed: Apr. 8, 1974

[21] Appl. No.: 458,611

[30] Foreign Application Priority Data

Apr. 12, 1973 United Kingdom .............. 17551/73

[52] U.S. Cl. 260/326.5 B; 260/251 A; 260/326.15; 424/251; 424/274

[51] Int. Cl.$^2$ ........................................ C07D 487/04

[58] Field of Search .................. 260/251 A, 326.5 B

[56] References Cited

OTHER PUBLICATIONS

Sherlin et al., Chemical Abstracts, Vol. 30, 2195[8] (1936).

Brown, The Pyrimidines, Interscience Publishers, N.Y., (1962), p. 449.

*Primary Examiner*—Nicholas S. Rizzo

*Assistant Examiner*—Diana G. Rivers

[57] ABSTRACT

The invention relates to a process for preparing fused ring indole derivatives of formula (I)

(I)

wherein $R^1$, $R^2$, $R^3$, $R^4$ are each hydrogen, hydroxyl, lower alkyl, lower alkoxy, haloloweralkyl or halogen, $R^5$ and $R^6$ are each hydrogen or lower alkyl and *m* and *n* are 0, 1, 2 or 3 and the sum of $m + n$ is 2 or 3, by condensing an indole derivative of formula (II)

with a dihaloalkane of formula $$Hal(CH_2)_m C(R^5)(R^6)-(CH_2)_n Hal'$$

The products have pharmacological activity, particularly antidepressant and hypoglycaemic activity.

6 Claims, No Drawings

PROCESS FOR THE PREPARATION OF DIAZEPINO[1,2-A]INDOLES

This invention relates to fused ring indole derivatives. More particularly it relates to a process for the preparation of certain pyrimido[1,2-a]indoles and diazepino[1,2-a]indoles and the products of this process.

German Offenlegungsschrift No. 2,200,584 discloses certain imidazo[1,2-a]indoles, pyrimido[1,2-a]indoles and diazepino[1,2-a]indoles and various processes for their preparation. We have now found that some of the compounds can be prepared by a novel alternative process.

Accordingly the present invention provides a process for the preparation of an indole derivative of the general formula (I)

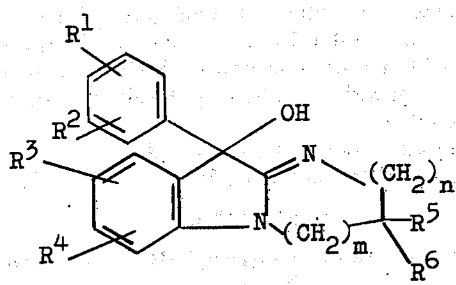

or an acid addition salt thereof, wherein $R^1$, $R^2$, $R^3$ and $R^4$ are each hydrogen,hydroxyl, lower alkyl, lower alkoxy, haloloweralkyl or halogen, $R^5$ and $R^6$ are each hydrogen or lower alkyl and *m* and *n* are 0, 1, 2 or 3 and the sum of $m + n$ is 2 or 3 which comprises condensing an indole derivative of general formula (II)

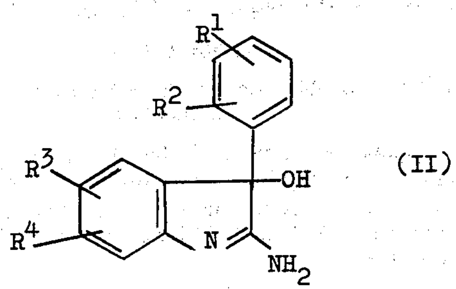

wherein $R^1$, $R^2$, $R^3$ and $R^4$ have the meanings given above with a dihaloalkane of general formula (III)

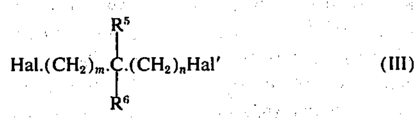

wherein $R^5$, $R^6$, *m* and *n* have the meanings given above and Hal and Hal' are each chlorine, bromine or iodine, and if desired converting a resulting acid addition salt to a free base or a free base to an acid addition salt.

The indole derivative of general formula (II) may exist in the alternative tautomeric form of general formula (II*a*)

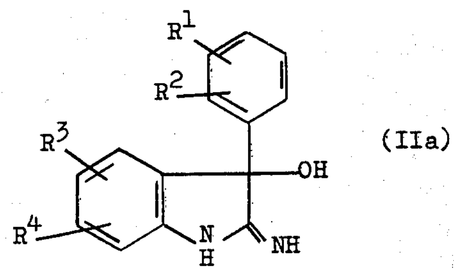

Where in this specification there is used a formula or name implying a structure of general formula (II) it is to be understood that this name or structure includes the tautomeric compound of general formula (II*a*) or a mixture of the two tautomers.

The term "lower" as used herein means that the radical contains up to 6 carbon atoms preferably up to 4 carbon atoms.

The following are examples of the groups $R^1$, $R^2$, $R^3$, $R^4$: hydrogen; hydroxyl; lower alkyl such as methyl, ethyl, propyl and butyl; lower alkoxy such as methoxy, ethoxy, propoxy and butoxy; haloloweralkyl, e.g., trifluoromethyl and halogen such as chlorine and bromine. Preferably each group $R^1$, $R^2$, $R^3$ and $R^4$ is hydrogen or at least one of the groups is halogen and the remaining groups are hydrogen.

The groups $R^5$ and $R^6$ are hydrogen or lower alkyl, e.g., methyl, ethyl, propyl and butyl. Preferably both groups $R^5$ and $R^6$ are hydrogen.

The compounds of general formula (I) in which the sum of $m + n$ is 2 are pyrimido[1,2-a]indoles and the compounds in which the sume of $m + n$ is 3 are 1,3-diazepino[1,2-a]indoles. Preferably *m* and *n* are 1 or 2, i.e., both are 1 or one is 1 and the other is 2.

The indole derivative (II) may be reacted with the dihaloalkane (III) in an inert organic solvent, i.e., a solvent which will dissolve the reactants but will not interfere with their interaction, e.g., dimethylformamide and alcohols such as ethanol and isopropanol. The reaction mixture may be heated, for example at the reflux temperature. A base, such as potassium carbonate or di-isopropylamine, can be added to the reaction mixture but this is not essential. The product can be obtained from the reaction medium by conventional methods. Isolation sometimes provides the indole derivative (I) in the form of its hydrohalic acid addition salt. The free base can be obtained in the usual manner by basifying a solution of the acid addition salt. The free base can be converted into acid addition salts, particularly pharmaceutically acceptable acid addition salts by dissolving the free base in a suitable organic solvent and treating it with a solution of the selected acid, in accordance with conventional procedures for preparing acid addition salts from base compounds. As examples of acids, there may be used hydrochloric, hydrobromic, tartaric, phosphoric, maleic, citric, methanesulphonic or p-toluene sulphonic acids.

In the dihaloalkane (III), the groups Hal and Hal' may be the same or different. If the groups are different the indole derivative (I) will be obtained as a mixture of hydrohalic acid addition salts from which the free base can be obtained by the process described above. Preferably the groups Hal and Hal' are the same. For example, they are both preferably bromine. The dihaloalkanes (III) are known compounds or can be prepared by methods described in the literature.

The indole derivative (II) may be prepared by the process described in U.S. Pat. No. 3,576,001 and by S. C. Bell et al., in J. Heterocyclic Chem., 1969, 6, 599–604. In this process the indole derivative is prepared by a process involving cyclization of a 2-benzoylacylanilide with an ionic cyanide such as potassium cyanide. The 2-benzoylacylanilides may be prepared by acylation of a 2-aminobenzophenone. The 2-aminobenzophenones are known compounds or may be prepared by methods described in the literature, for example in J. Am. Chem. Soc., 1943, 65, 363 or J. Heterocyclic Chem., 1971, 8, 903–910.

The compounds of formula (I) possess at least one asymmetric carbon atom and hence optical enantiomorphs are possible and the compounds may be obtained as the pure enantiomorphs or mixtures of such enantiomorphs, such as the racemates. The pure enantiomorphs may be obtained by the process of the present invention by employing optically active starting materials. Alternatively, a racemic mixture of the compound of general formula (I) may be resolved by the process described in German Offenlegungsschrift No. 2,200,584.

As described in the last mentioned specification, the compounds of general formula (I) exhibit pharmacological activity, e.g., antidepressant, anti-inflammatory, anti-histaminic, cardiovascular, diuretic or hypoglycaemic activity. Examples of specific compounds having good antidepressant activity when tested by standard pharmacological tests are 2,3,4,10-tetrahydro-10-phenyl-pyrimido[1,2-a]indol-10-ol, 10-(m-chlorophenyl)-2,3,4,10-tetrahydropyrimido[1,2-a]indol-10-ol and 2,4,5,11-tetrahydro-11-phenyl-3H-1,3-diazepino[1,2-a]indol-11-ol. The last compound also has good hypoglycaemic activity.

The following examples illustrate the invention:

EXAMPLE 1

2,3,4,10-Tetrahydro-10-phenylpyrimido[1,2-a]indol-10-ol.

a. Dichloroacetylchloride (88 ml) in dichloromethane (200 ml) was added dropwise to a stirred solution of 2-aminobenzophenone (157.6g) in dichloromethane (400 ml) and triethylamine (116 ml) while keeping the temperature between 20°–30°C by cooling in ice. On completion of the addition the reaction was stirred at room temperature for 1.5 hours. The reaction mixture was washed with successive portions of distilled water-dilute hydrochloric acid and finally distilled water. After drying over anhydrous magnesium sulphate the solvent was removed under reduced pressure to leave a solid which on recrystallisation from absolute, ethanol gave 222 g of 2'-benzoyl-2,2-dichloroacetanilide, m.p. 112°–114°C.

Analysis: Found C, 58.5; H, 3.7; N, 4.5. $C_{15}H_{11}Cl_2NO_2$ requires C, 58.5; H, 3.6; N, 4.5%.

b. 2'-Benzoyl-2,2-dichloroacetanilide (50 g.) was suspended in 91% ethanol (750 ml) and treated with a solution of potassium cyanide (30 g) in water (50 ml). The reaction was stirred at room temperature for 40 hours. The crystalline precipitate was filtered off and the mother liquors diluted with water to provide further crops of 2-amino-3-phenyl-3H-indol-3-ol. Total 37 g. The product could be recrystallized from acetonitrile or aqueous dimethylformamide and had a m.p. of 204°–6°C (decomp).

Analysis: Found C, 75.0; H, 5.4; N, 12.5. $C_{14}H_{12}N_2O$ requires C, 74.9; H, 5.6; N, 12.4%.

c. 2-Amino-3-phenyl-3H-indol-3-ol (2.24 g) was heated under reflux with isopropanol (20 ml) and 1,3-dibromopropane (2.0 g) for 20 hours. The reaction mixture was evaporated to 10 ml and diluted with a little ether. The title compound was obtained as its hydrobromide salt 0.73 g., m.p. 260°–262°C (decomp.) and could be recrystallized from methanol, ethanol or isopropanol with or without the addition of ethyl acetate or ether.

Analysis: Found C, .58.7; H, 5.1; N, 7.8. $C_{17}H_{16}N_2O.HBr$ requires C, 59.15; H, 4.8; N, 8.1%

EXAMPLE 2

2,4,5,11-Tetrahydro-11-phenyl-3H-1,3-diazepino[1-,2a]indol-11-ol

2Amino-3-phenyl-3H-indol-3-ol (8.96 g) was heated under reflux with 1,4-dibromobutane (8.64 g) in absolute ethanol (65 ml) for 30 hours. The reaction mixture was evaporated to small bulk and allowed to recrystallize. The product was obtained as its hydrobromide salt(4.67 g) m.p. 270°–272° (decomp.) and could be recrystallized from ethanol m.p. 262°–277°C (decomp.).

Analysis: Found C, 60.6; H, 5.5; N, 7.8% $C_{18}H_{18}N_2O.HBr$ requires C, 60.3; H, 5.3; N, 7.8%.

EXAMPLE 3

8-Chloro-2,3,4,10-tetrahydro-10-phenylpyrimido[1,2-a]indol-10-ol

Reaction of 2-amino-5-chloro-3-phenyl-3H-indol-3-ol (2.58 g) with 1,3-dichloropropane (1.1 g) according to the procedure of Example 1 step (c) gives the title compound as its hydrochloride salt, m.p. 279°–282°C (decomp).

EXAMPLE 4

2,3,4,10-Tetrahydro-2(and 4)-methyl-10-phenyl-pyrimido[1,2-a]indol-10-ol

2-Amino-3-phenyl-3H-indol-3-ol (2.24 g) was heated under reflux with 1,3-dibromobutane (2.16 g) in absolute ethanol (10 ml) for 16 hours. On cooling colourless needles, believed to be 2-ethoxy-3-phenyl-3H-indol-3-ol, (500 mg m.p. 197°–199°C) were obtained. These were discarded. The mother liquors were evaporated under reduced pressure to a foam which was redissolved in hot isopropanol. On cooling 697 mg of a mixture of the hydrobromides of the title compounds was obtained, m.p. 270°–272°C (decomp.) after recrystallization from ethanol/ether.

Analysis: Found C, 60.1; H, 5.4; N, 7.7. $C_{18}H_{18}N_2O$ HBr requires C, 60.3; H, 5.3; N, 7.8%.

EXAMPLE 5

11-(m-Chlorophenyl)-2,4,5,11-tetrahydro-3H-1,3-diazepino[1,2-a]indol-11-ol a. 2-Amino-3'-chlorobenzophenone (6.12 g) was stirred and cooled at 15°C in solution in acetone (25 ml) while dichloroacetyl chloride (4.86 g) was added dropwise. After stirring at room temperature for 20 minutes the reaction mixture was poured into water, the acetone was removed under reduced pressure and the resulting oil extracted into chloroform. After drying over magnesium sulphate the chloroform was removed under reduced pressure and the product crystallized from ethanol. 2'-(m-Chlorobenzoyl)-2,2-dichloroacetanilide was obtained as yellow needles (6.88 g), m.p. 73°–75°C after recrystallization from ethanol.

Analysis: Found C, 52.8; H, 2.9; N, 4.1. $C_{15}H_{10}Cl_3NO_2$ requires C, 52.6; H, 2.9; N, 4.1%.

b. The dichloroacetanilide obtained above was dissolved in ethanol (150 ml) and treated with a solution of potassium cyanide (6 g) in water (50 ml). After stirring at room temperature overnight the reaction mixture was treated with charcoal, filtered and the ethanol removed under reduced pressure. The resulting oil was extracted into chloroform, dried over magnesium sulphate and evaporated to an oil which afforded 4.6 g of 2-amino-3-(m-chlorophenyl)-3H-indol-3-ol, m.p. 247°–250°C (decomp.), as its hydrochloride on treatment with isopropanol and hydrogen chloride in dry ether.

Analysis: Found C, 57.1; H, 4.1; N, 9.1. $C_{14}H_{11}ClN_2O$ requires C, 56.9; H, 4.1; N, 9.4%.

c. 2-Amino-3-(m-chlorophenyl)-3H-indol-3-ol hydrochloride (8.66 g) was converted to its oily base then heated under reflux with 1,4-dibromobutane (6.35 g) in ethanol (20 ml) for 4 hours. On cooling the title compound was obtained as its hydrobromide salt (2.41 g) m.p. 270°–275° C (decomp.) after recrystallization from methanol/ethyl acetate.

Analysis: Found C, 54.85; H, 4.6; N, 7.1. $C_{18}H_{17}ClN_2O$ HBr requires C, 54.9; H, 4.35; N, 7.1%.

EXAMPLE 6

10-(m-Chlorophenyl)-2,3,4,10-tetrahydropyrimido[1,2-a]indol-10-ol

2-Amino-3-(m-chlorophenyl)-3H-indol-3-ol hydrochloride (2.3 g) is converted to its oily base then heated under reflux in ethanol (10 ml) with 1,3-dibromopropane (1.55 g) for 20 hours. On cooling the title compound is obtained as its hydrobromide, m.p. 270°–273°C (decomp.).

EXAMPLE 7

9-Chloro-11-(o-chlorophenyl)-2,4,5,11-tetrahydro-3H-1,3-diazepino[1,2-a]indol-11-ol a. Dichloroacetyl chloride (17 ml) in dichloromethane (50 ml) was added dropwise to a stirred solution of 2-amino-2',5-dichlorobenzophenone (40.8 g) and triethylamine (24 ml) in dichloromethane (100 ml). The mixture was stirred for 15 hours at room temperature and washed with water. After drying over magnesium sulphate the solvent was removed under reduced pressure and the resulting oil crystallized from ethanol, affording 48.14 g of colourless crystals, m.p. 130°–133°C after recrystallization from ethanol.

Analysis: Found c, 48.2; H, 2.5; N, 3.9. $C_{15}H_9Cl_4NO_2$ requires C, 47.8; H, 2.4; N, 3.7% b. The dichloroacetanilide obtained in (a) above was dissolved in 90% ethanol (500 ml) and stirred for 24 hours at room temperature with potassium cyanide (20.95 g) in water (180 ml). The undissolved material was filtered and the filtrate diluted with water yielding 28.74 g of 2-amino-5-chloro-3-(o-chlorophenyl)-3H-indol-3-ol, m.p. 146°–148°C after recrystallization from aqueous dimethylformamide.

c. 2-Amino-5-chloro-3-(o-chlorophenyl)-3H-indol-3-ol (5.86 g) was heated under reflux with 1,4-dibromobutane (4.32 g) for 18 hours. On cooling the hydrobromide of the title compound (1.67 g) was deposited m.p. 295°–300°C (decomp.).

Analysis: Found C, 50.3; H, 4.05; N, 6.4. $C_{18}H_{16}Cl_2N_2O.HBr$ requires C, 50.5; H, 4.0; N, 6.5%.

EXAMPLE 8

9-Chloro-11-phenyl-2,4,5,11-tetrahydro-3H-1,3-diazepino[1,2-a]indol-11-ol a. Potassium cyanide (18 g) in water (150 ml) was added to a suspension of 2'-benzoyl-2,2,4'-trichloroacetanilide (30 g) in ethanol (400 ml). The reaction was stirred overnight and after treatment with charcoal diluted with water, 2-Amino-5-chloro-3-phenyl-3H-indol-3-ol (19.57 g) was obtained as off white crystals m.p. 205°–208°C after recrystallization from acetonitrile.

b. 2-Amino-5-chloro-3-phenyl-3H-indol-3-ol (5.16 g) was heated under reflux with 1,4-dibromobutane (4.32 g) for 24 hours. After cooling the solid was filtered off affording 1.88 g of the title compound as its hydrobromide, m.p. 298°–300°C (decomp.) after recrystallization from methanol/ethyl acetate.

Analysis: Found C, 54.5; H, 4.6; N, 7.0. $C_{18}H_{17}ClN_2O.HBr$ requires C, 54.9; H, 4.35, N, 7.1%.

We claim:

1. A process for the preparation of an indole derivative selected from the group consisting of a compound of the formula (I)

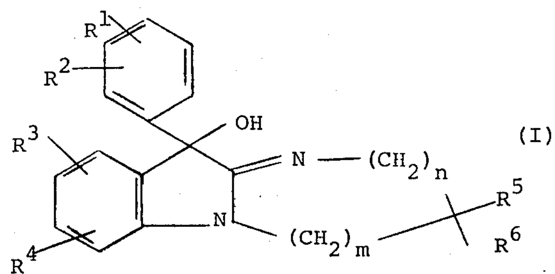

and an acid addition salt thereof, wherein $R^1$, $R^2$, $R^3$ and $R^4$ are selected independently from the group consisting of hydrogen, hydroxyl, lower alkyl containing 1 to 4 carbon atoms, lower alkoxy containing 1 to 4 carbon atoms, trifluoromethyl, and halogen, $R^5$ and $R^6$ are selected independently from the group consisting of hydrogen and lower alkyl containing 1 to 4 carbon atoms and $n$ and $m$ are selected from the group consisting of 1 and 2 such that the sum of $m + n$ is 3, which process comprises condensing an indole derivative of formula (II)

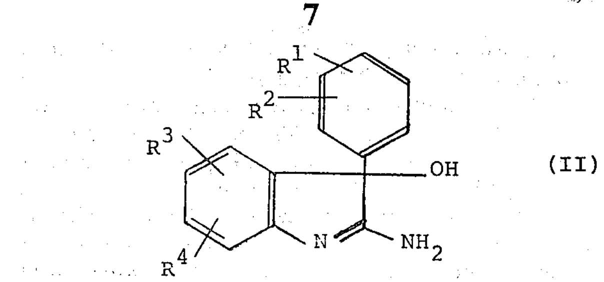

wherein $R^1$, $R^2$, $R^3$ and $R^4$ have the meanings given above with a dihaloalkane of formula (III)

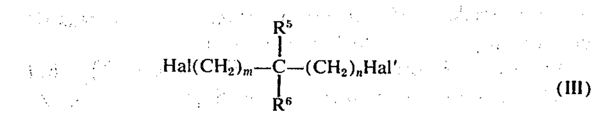

where $R^5$, $R^6$, $m$ and $n$ have the meanings given above and Hal and Hal' are each chlorine or bromine.

2. A process according to claim 1 wherein the condensation is carried out by heating the indole derivative of formula (II) with the dihaloalkane of formula (III) in an inert organic solvent.

3. A process according to claim 1 for preparing 2,4,5,11-tetrahydro-11-phenyl-3H-1,3-diazepino[1,2-a]indol-11-ol which comprises heating 2-amino-3-phenyl-3H-indol-3-ol with 1,4-dibromobutane in an inert organic solvent.

4. A process according to claim 1 for preparing 11-(m-chlorophenyl)-2,4,5,11-tetrahydro-3H-1,3-diazepino[1,2-a]indol-11-ol which comprises heating 2-amino-3-(m-chlorophenyl)-3H-indol-3-ol with 1,4-dibromobutane in an inert organic solvent.

5. A process according to claim 1 for prearing 9-chloro-11-(o-chlorophenyl)-2,4,5,11-tetrahydro-3H-1,3-diazepino[1,2-a]indol-11-ol which comprises heating 2-amino-5-chloro-3-(o-chlorophenyl)-3H-indol-3-ol with 1,4-dibromobutane in an inert organic solvent.

6. A process according to claim 1 for preparing 9-chloro-11-phenyl-2,4,5,11-tetrahydro-3H-1,3-diazepino[1,2-]indol-11-ol which comprises heating 2-amino-5-chloro-3-phenyl-3H-indol-3-ol with 1,4-dibromobutane in an inert organic solvent.

* * * * *